United States Patent [19]

Blenk et al.

[11] Patent Number: 5,573,766
[45] Date of Patent: Nov. 12, 1996

[54] BACILLUS THURINGIENSIS STRAINS PRODUCING INSECTICIDALLY ACTIVE TOXINS

[75] Inventors: Robert G. Blenk, Sunnyvale, Calif.; Susan Ely, Marlow, England; Ravindra H. Tailor, Berkshire, England; Janet M. Tippett, Reading, England

[73] Assignee: Imperial Chemical Industries PLC, London, England

[21] Appl. No.: 520,228

[22] Filed: May 9, 1990

[30] Foreign Application Priority Data

May 9, 1989 [GB] United Kingdom .................. 8910624

[51] Int. Cl.$^6$ ............................. A01N 63/02; A61K 39/07
[52] U.S. Cl. .................. 424/93.461; 424/246.1; 435/832; 504/117
[58] Field of Search .............................. 435/69.1, 252.31, 435/832; 424/932, 246.1, 93.461

[56] References Cited

PUBLICATIONS

Aronson et al. Microbiol. Rev. 50(1):1–24 (1986).

Primary Examiner—John L. LeGuyader
Attorney, Agent, or Firm—Cushman Darby & Cushman, L.L.P.

[57] ABSTRACT

Novel strains of the insecticidal microorganism *Bacillus thuringiensis* are described. These contain novel genes, and in particular a gene coding for a novel insecticidal endotoxin, 81 kiloDaltons in length, toxic to both Lepidoptera and Coleoptera. The novel strains and the genes they contain may be used to combat insect attack against plants.

8 Claims, 26 Drawing Sheets

```
                                N           M                           H                                           48
                                D           S                           P
                                E           E                           H
                                1           1                           1
CAT ATG TAT AGA GCA ACT TAA TCA AGC AGA GAT ATT TTC ACC TAT CGA
His Met Tyr Arg Ala Thr Ter Ser Ser Arg Asp Ile Phe Thr Tyr Arg
 1               5                  10                  15

96
TGA AAA TAT CTC TGC TTT TTC TTT TAT TTG GTA TAT GCT TTA CTT
Ter Lys Tyr Leu Cys Phe Phe Phe Tyr Leu Val Tyr Ala Leu Leu
         20                  25                  30

A
        T
        Q
        1
                                                                                                                   144
GTA ATC GAA AAT AAA GCA CTA ATA AGA GTA TTT ATA GGT GTT TGA AGT
Val Ile Glu Asn Lys Ala Leu Ile Arg Val Phe Ile Gly Val Ter Ser
             35                  40                  45

```
                                                        M D   M
                                              M D       S R   A
                                              S R       E A   E
                                              E A       1 1   2
                          S                   1 1
                          S
                          P
                          1
TAT TTC AGT TCA TTT TTA AAG AAG GTT TAA AGA CGT TAG AAA GTT ATT       192
Tyr Phe Ser Ser Phe Leu Lys Lys Val Ter Arg Arg Ter Lys Val Ile
 50              55                  60
                                                        A M
                                                        S S
                                                        E E
                                                        1 1
                                                          /
AAG GAA TAA TTA TTA GTA AAT TCC ACA TAT ATT ATA TAA ATT       240
Lys Glu Ter Tyr Leu Leu Val Asn Ser Thr Tyr Ile Ile Ter Leu Ile
 65              70                  75                  80
                                                        A D
                                                        L D
                                                        U E
                                                        1 1
ATG AAA TAT ATG TAT AAA TTG AAA ATG CTT TAT TTG ACA TTA CAG CTA       288
Met Lys Tyr Met Tyr Lys Leu Lys Met Leu Tyr Leu Thr Leu Gln Leu
             85                  90                  95
```

```
                                              MseI
                                              |
AGT ATA ATT TTG TAT GAA TAA TAT ATC TGA AAA TTA AAT AAT AGT    336
Ser Ile Ile Leu Tyr Glu Ter Tyr Ile Ter Lys Leu Asn Asn Ser
        100                 105                 110

SboI   AseI
         |      |
         |      HinfI
         |      |
ATA AGT GGA GGG ATT AAT ATG AAA CTA AAG AAT CAA GAT AAG CAT CAA    384
Ile Ser Gly Gly Ile Asn Met Lys Leu Lys Asn Gln Asp Lys His Gln
            115                 120                 125

MaeI                              HinfI
     |                                 |
AGT TTT TCT AGC AAT GCG AAA GTA GAT AAA ATC TCT ACG GAT TCA CTA    432
Ser Phe Ser Ser Asn Ala Lys Val Asp Lys Ile Ser Thr Asp Ser Leu
                135                 140

FIG. 5C
```

```
                                    A M        B              N
                                    S S        S              L
                                    E E        P              A
                                    1 1        H              3
                                     /
AAA AAT GAA ACA GAT ATA GAA TTA CAA AAC ATT AAT CAT GAA GAT TGT    480
Lys Asn Glu Thr Asp Ile Glu Leu Gln Asn Ile Asn His Glu Asp Cys
145                 150                 155                 160

M       D
    B       D
    O       E
    2       1

TTG AAA ATG TCT GAG TAT GAA AAT GTA GAG CCG TTT GTT AGT GCA TCA    528
Leu Lys Met Ser Glu Tyr Glu Asn Val Glu Pro Phe Val Ser Ala Ser
        165                 170                 175

BAN RKS ASN
    S                                           ASL SPT WEA
    F                                           NPA ANY RCE
    A                                           114 111 211
    N                                            /   /   ///
ACA ATT CAA ACA GGT ATT GGT ATT GCG GGT AAA ATA CTT GGT ACC CTA    576
Thr Ile Gln Thr Gly Ile Gly Ile Ala Gly Lys Ile Leu Gly Thr Leu
            180                 185                 190
```

FIG. 5D

```
                                      E                                  A H                                              624
                                      C                                  L A
                                      O                                  U E
                                      1                                  1 1                                D
                                                                                                            D
                                                                                                            E
                                                                                                            1
GGC GTT CCT TTT GCA GGA CAA GTA GCT AGT CTT TAT AGT TTT ATC TTA
Gly Val Pro Phe Ala Gly Gln Val Ala Ser Leu Tyr Ser Phe Ile Leu
        195                     200                 205

A     H H   H M D                                                                    A
              L     A P   A S D                                                                    F
              V     E H   E T E                                                                    L
              1     1 1   3 2 1                                                                    3
                          / / /
GGT GAG CTA TGG CCT AAG GGG AAA AAT CAA TGG GAA ATC TTT ATG GAA       672
Gly Glu Leu Trp Pro Lys Gly Lys Asn Gln Trp Glu Ile Phe Met Glu
        210                 215                 220

N N K   E             A M   M
    S L S   A             S S   B
    P A P   R             E E   O
    H 3 2   1             1 1   2
    / /                   /
CAT GTA GAA GAG ATT ATT AAT CAA AAA ATA TCA ACT TAT GCA AGA AAT       720
His Val Glu Glu Ile Ile Asn Gln Lys Ile Ser Thr Tyr Ala Arg Asn
        225                 230                 235             240
```

FIG. 5E

```
                                                              S            D  A  A
                                                              F            D  L  C
                                                              A            E  U  C
                                                              N            1  1  1
AAA GCA CTT ACA GAC TTG AAA GGA TTA GGA GAT GCC TTA GCT GTC TAC         768
Lys Ala Leu Thr Asp Leu Lys Gly Leu Gly Asp Ala Leu Ala Val Tyr
             245                 250                 255

N  H                                                                  M
     H  N                                                                  A
     L  F                                                                  E
     A  3                                                                  1
     F
     31
CAT GAT TCG CTT GAA AGT TGG GTT GGA AAT CGT AAT AAC ACA AGG GCT         816
His Asp Ser Leu Glu Ser Trp Val Gly Asn Arg Asn Asn Thr Arg Ala
             260                 265                 270

AGG AGT GTT GTC AAG AGC CAA TAT ATC GCA TTA GAA TTG ATG TTC GTT         864
Arg Ser Val Val Lys Ser Gln Tyr Ile Ala Leu Glu Leu Met Phe Val
             275                 280                 285
```

FIG. 5F

```
                                      B  ANR K
                                      A  SLS P
                               M  AM  N  PAA N
                               N  LN  1  141 1
                               L  WL  /  /  /
                               1  H1
CAG AAA CTA CCT TCT TTT GCA GTG TCT GGA GAG GAG GTA CCA TTA TTA    912
Gln Lys Leu Pro Ser Phe Ala Val Ser Gly Glu Glu Val Pro Leu Leu
    290                 295                 300

S   M
          B             A F                   F   S
          B             L N                   A   E
          V             U U                   N   1
          1             1 H
CCG ATA TAT GCC CAA GCT GCA AAT TTA CAT TTG CTA TTA AGA GAT        960
Pro Ile Tyr Ala Gln Ala Ala Asn Leu His Leu Leu Leu Arg Asp
    305                 310                 315                 320

N   S                                 M
    S   F                                 B
    1   A                                 O
    1   N                                 2
    3
    /
GCA TCT ATT TTT GGA AAA GAG TGG GGA TTA TCA TCT TCA GAA ATT TCA   1008
Ala Ser Ile Phe Gly Lys Glu Trp Gly Leu Ser Ser Ser Glu Ile Ser
                    325                 330                 335
```

FIG.5G

```
ACA TTT TAT AAC CGT CAA GTC GAA CGA GCA GGA GAT TAT TCC TAC CAT      1056
Thr Phe Tyr Asn Arg Gln Val Glu Arg Ala Gly Asp Tyr Ser Tyr His
        340             345             350
                            T               E       R
                            A               C       S
                            Q               P       A
                            1               1       1
                                            M
                                            N
                                            L
                                            1

TGT GTG AAA TGG TAT AGC ACA GGT CTA AAT AAC TTG AGG GGT ACA AAT      1104
Cys Val Lys Trp Tyr Ser Thr Gly Leu Asn Asn Leu Arg Gly Thr Asn
        355             360             365
            R                       B           N
            S                       S           L
            A                       M           A
            1                       2           3
                                                M
                                                S
                                                E
                                                1

GCC GAA AGT TGG GTA CGA TAT AAT CAA TTC CGT AGA GAC ATG ACT TTA      1152
Ala Glu Ser Trp Val Arg Tyr Asn Gln Phe Arg Arg Asp Met Thr Leu
        370             375             380
```

```
ECOD1  RSA1  MAE1                                                    ALU1
ATG GTA CTA GAT TTA GTG GCA CTA TTT CCA AGC TAT GAT ACA CAA ATG   1200
Met Val Leu Asp Leu Val Ala Leu Phe Pro Ser Tyr Asp Thr Gln Met
385                 390                 395                 400

MSE1              FOK1  HF I F R  SFA1  RSA1
TAT CCA ATT AAA ACT ACA GCC CAA CTT ACA AGA GAA GTA TAT ACA GAC   1248
Tyr Pro Ile Lys Thr Thr Ala Gln Leu Thr Arg Glu Val Tyr Thr Asp
                405                 410                 415

GCA ATT GGG ACA GTA CAT CCG CAT CCA AGT TTT ACA AGT ACG ACT TGG   1296
Ala Ile Gly Thr Val His Pro His Pro Ser Phe Thr Ser Thr Thr Trp
                420                 425                 430
```

```
                                      B   B M                  B F E A
                                      B   N L                  G N C S
                                      V   L 1                  L U 1 U
                                      1   1                    1 H 5 2
TAT AAT AAT AAT GCA CCT TCG TTC TCT GCC ATA GAG GCT GCT GTT GTT          1344
Tyr Asn Asn Asn Ala Pro Ser Phe Ser Ala Ile Glu Ala Ala Val Val
            435                 440                 445

T S       X M           M              A
                                A F       B A           A              L
                                Q A       A E           E              U
                                1 N       1 1           3              1
T
A
Q
1
CGA AAC CCG CAT CTA CTC GAT TTT CTA GAA CAA GTT ACA ATT TAC AGC          1392
Arg Asn Pro His Leu Leu Asp Phe Leu Glu Gln Val Thr Ile Tyr Ser
            450                 455                 460

M   T              M           D                       M
 S   A              A           D                       K
 E   Q              E           E                       L
 1   1              3           1                       1
TTA TTA AGT CGA TGG AGT AAC ACT CAG TAT ATG AAT ATG TGG GGA GGA          1440
Leu Leu Ser Arg Trp Ser Asn Thr Gln Tyr Met Asn Met Trp Gly Gly
            465                 470                 475             480
```

FIG. 5J

```
                    M           M
                    A           N
                    E           L
                    1           1
                                                                                                              M M
                                                                                                              A S
                                                                                                              E E
                                                                                                              2 1
CAT AAA CTA GAA TTC CGA ACA ATA GGA GGA ACG TTA AAT ATC TCA ACA              1488
His Lys Leu Glu Phe Arg Thr Ile Gly Gly Thr Leu Asn Ile Ser Thr
            485                     490                     495

B XMD                                                              M
  1 HBP                                                              A
  N OON                                                              E
  1 211                                                              3
    /
              AM
              SS
              EE
              11
               /
CAA GGA TCT ACT AAT ACT TCT ATT AAT CCT GTA ACA TTA CCG TTC ACT              1536
Gln Gly Ser Thr Asn Thr Ser Ile Asn Pro Val Thr Leu Pro Phe Thr
            500                     505                     510

XA TB    AM A                                  H              H
  HV AS    HA A                                  N              N
  OA QM    AE T                                  F              F
  11 12    22 2                                  1              1
   /  /     /
TCT CGA GAC GTC TAT AGG ACT GAA TCA TTG GCA GGG CTG AAT CTA TTT              1584
Ser Arg Asp Val Tyr Arg Thr Glu Ser Leu Ala Gly Leu Asn Leu Phe
            515                     520                     525

FIG. 5K
```

```
                              M                      R SAS M       S   M S   F
                              S                      S TVE A       P   S P   O
                              E                      A YRC E       O   E O   K
                              1                      1 121 1       1   1 1   1

TTA ACT CAA CCT GTT AAT GGA GTA CCT AGG GTT GAT TTT CAT TGG AAA   1632
Leu Thr Gln Pro Val Asn Gly Val Pro Arg Val Asp Phe His Trp Lys
530             535             540

M   M DP              S                         TE SAS
        H   B PV              F                         TC EPC
        N   N NU              A                         HR CYR
        F   O 1 1             N                         22 111
        3                                                  /

TTC GTC ACA CAT CCG ATC GCA TCT GAT AAT TTC TAT TAT CCA GGG TAT   1680
Phe Val Thr His Pro Ile Ala Ser Asp Asn Phe Tyr Tyr Pro Gly Tyr
545             550             555             560

F H   H
            I G   N
            N A   F
            1 1   1

GCT GGA ATT GGG ACG CAA TTA CAG GAT TCA GAA AAT GAA TTA CCA CCT   1728
Ala Gly Ile Gly Thr Gln Leu Gln Asp Ser Glu Asn Glu Leu Pro Pro
565             570             575
```

FIG.5L

```
GAA GCA ACA GGA CAG CCA AAT TAT GAA TCT TAT AGT CAT AGA TTA TCT    1776
Glu Ala Thr Gly Gln Pro Asn Tyr Glu Ser Tyr Ser His Arg Leu Ser
            580                 585                 590

P   H                           A   SNN
    L   N                           F   FSL
    E   F                           L   APA
    1   1                           3   NH3
                                        //
CAT ATA GGA CTC ATT TCA GCA TCA CAT GTG AAA GCA TTG GTA TAT TCT    1824
His Ile Gly Leu Ile Ser Ala Ser His Val Lys Ala Leu Val Tyr Ser
            595                 600                 605

H   S   M   D   R   S   A
            G   F   B   P   S   A
            A   A   O   N   A
            1   N   1   1   1

TGG ACG CAT CGT AGT GCA GAT CGT ACA AAT ACA ATT GAG CCA AAT AGC    1872
Trp Thr His Arg Ser Ala Asp Arg Thr Asn Thr Ile Glu Pro Asn Ser
        610                 615                 620
```

ATT ACA CAA ATA CCA TTA GTA AAA GCT TTC AAT CTG TCT TCA GGT GCC          1920
Ile Thr Gln Ile Pro Leu Val Lys Ala Phe Asn Leu Ser Ser Gly Ala
625                 630                 635                 640

N  M           A  A  E            A  S                     E        A  T
    S  N           V  S  C            P  C                     C        S  A
    P  L           A  U  R            Y  R                     R        U  Q
    B  1           2  1  2            1  1                     V        2  1

GCT GTA GTG AGA GGA TTT ACA GGT GGG GAT ATC CTT CGA AGA                   1968
Ala Val Val Arg Gly Phe Thr Gly Gly Asp Ile Leu Arg Arg
            645                 650                 655

H   M           R  S  A                               S   A  M
    N   B           S  S                                  S   S  S
    F   O           A                                     P   E  E
    3   2           1                                     1   1  1

ACG AAT ACT GGT ACA TTT GGG GAT ATA CGA GTA AAT ATT AAT CCA CCA           2016
Thr Asn Thr Gly Thr Phe Gly Asp Ile Arg Val Asn Ile Asn Pro Pro
            660                 665                 670
```

```
                EM    T    H    H    H
                CN    H    N    N    N
                RL    A    F    F    F
                V1    1    1    1    3
                 \                   /
TTT GCA CAA AGA TAT CGC GTG AGG ATT CGC TAT GCT TCT ACC ACA GAT   2064
Phe Ala Gln Arg Tyr Arg Val Arg Ile Arg Tyr Ala Ser Thr Thr Asp
675                 680                 685

A   AM
         M                    M               L   SS
         A                    S               U   EE
         E                    E               1   11
         2                    1                    /
TTA CAA TTC CAT ACG TCA ATT AAC GGT AAA GCT ATT AAT CAA GGT AAT   2112
Leu Gln Phe His Thr Ser Ile Asn Gly Lys Ala Ile Asn Gln Gly Asn
690                 695                 700

D
         M         M                          D
         N         N                          E
         L         L                          1
         1         1
TTT TCA GCA ACT ATG AAT AGA GGA GAG GAC TTA GAC TAT AAA ACC TTT   2160
Phe Ser Ala Thr Met Asn Arg Gly Glu Asp Leu Asp Tyr Lys Thr Phe
705                 710                 715                 720
```

FIG. 5P

```
                                                              ALU1         RSA1    RSA1
AGA ACT GTA GGC TTT ACC ACT CCA TTT AGC TTT TTA GAT GTA CAA AGT      2208
Arg Thr Val Gly Phe Thr Thr Pro Phe Ser Phe Leu Asp Val Gln Ser
            725                 730                 735

MBO2                    KSPM
                                                SAAE
                                                PRA
                                                2 13
ACA TTC ACA ATA GGT GCT TGG AAC TTC TCT TCA GGT AAC GAA GTT TAT      2256
Thr Phe Thr Ile Gly Ala Trp Asn Phe Ser Ser Gly Asn Glu Val Tyr
            740                 745                 750

XMN1        HPA2        MAE3    MNL1    NDE1
ATA GAT AGA ATT GAA TTT GTT CCG GTA GAA GTA ACA TAT GAG GCA GAA      2304
Ile Asp Arg Ile Glu Phe Val Pro Val Glu Val Thr Tyr Glu Ala Glu
            755                 760                 765
```

FIG. 5Q

```
                                    H H                    M
                                    I H                    A
                                    N A                    E
                                    P 1                    3
TAT GAT TTT GAA AAA GCG CAA GAG AAG GTT ACT GCA CTG TTT ACA TCT    2352
Tyr Asp Phe Glu Lys Ala Gln Glu Lys Val Thr Ala Leu Phe Thr Ser
        770                 775                 780

H H M                           M                               E
M N N                           S                               C
F F L                           E                               R
3 1 1                           1                               2
ACG AAT CCA AGA GGA TTA AAA ACA GAT GTA AAG GAT TAT CAT ATT GAC    2400
Thr Asn Pro Arg Gly Leu Lys Thr Asp Val Lys Asp Tyr His Ile Asp
785             790                 795                 800

A S                         H       B P             E C
P C                         N       S L             C D
Y R                         F       M E             R X
1 1                         1       2 1             1
CAG GTA TCA AAT TTA GTA GAG TCT CTA TCA GAT GAA TTC TAT CTT GAT    2448
Gln Val Ser Asn Leu Val Glu Ser Leu Ser Asp Glu Phe Tyr Leu Asp
                805                 810                 815
```

```
                                                                    T  H
                                                                    A  
                                                                    Q  
                                                                    1                    M     T  H
                                                                                          S     H  
                                                                                          E     A  
                                                                                          1     1
GAA AAG AGA GAA TTA TTC GAG ATA GTT AAA TAC GCG AAG CAA CTC CAT      2496
Glu Lys Arg Glu Leu Phe Glu Ile Val Lys Tyr Ala Lys Gln Leu His
         820             825                 830

M   A   N  N     M
            A   F   S  L     S
            E   L   P  A     E
            3   3   H  3     1
                       /
ATT GAG CGT AAC ATG TAG AAT TAA AAT CTA CCT AAA TCC AGA AAA ATA     2544
Ile Glu Arg Asn Met Ter Asn Ter Asn Leu Pro Lys Ser Arg Lys Ile
         835             840                 845

M                         R  S
            S                         S  S
            E                         A  P
            1                         1  1
AAA GGG TTA AAT ATA CAA TTC TTG TAC CAA TAT TTT GAG TGA TTA GAT     2592
Lys Gly Leu Asn Ile Gln Phe Leu Tyr Gln Tyr Phe Glu Ter Leu Asp
         850             855                 860

FIG. 5R
```

```
                     MSE1                    MFO      MSE1                    MSE1
                                             K1
GTA GGA TGA AAT TTA ATT GTA TGC TAT TTA ACA GTA GAG ATA TTA AAA    2640
Val Gly Ter Asn Leu Ile Val Cys Tyr Leu Thr Val Glu Ile Leu Lys
865                 870                 875                 880

AM                            AM
SS                            SS
EE                            EE
11                            11
 \                             \
ATT AAT TTA TCT ATA CAT TAA TAG TAT AGA CAT ACA AAC ATA AGA GAG    2688
Ile Asn Leu Ser Ile His Ter Ter Tyr Arg His Thr Asn Ile Arg Glu
            885                 890                 895

CAT TGT CTT TTC GTA GGC TAC AAT GCT CTC TAT TTA CTA TTT ATT TTT    2736
His Cys Leu Phe Val Gly Tyr Asn Ala Leu Tyr Leu Leu Phe Ile Phe
                900                 905                 910
```

CTT TTG TAT CTT CAA ATT GAC GTT GTT CTA AGC GTT CTA TTG CAG CTC    2784
Leu Leu Tyr Leu Gln Ile Asp Val Val Leu Ser Val Leu Leu Gln Leu
        915             920             925

B
        B
        V
        1

GTC GTT TAG TAT CAT CAA TGT TTG TAT AAA GAG ATG TTG TTT CCA TAG    2832
Val Val Ter Tyr His Gln Cys Leu Tyr Lys Glu Met Leu Phe Pro Ter
        930             935             940

F
    I
    N
    1

AAT TAT GTC CCA TTT GAT TTG CTA ATA ATA CTA AAT CTT TAT TTT CAT    2880
Asn Tyr Val Pro Phe Asp Leu Leu Ile Ile Leu Asn Leu Tyr Phe His
        945             950             955             960
```

FIG.5T

```
TAT AGT GAT TAG TAG CAT AAG TAT GAC GTA ATT TAT GAG GGC TTT TCT   2928
Tyr Ser Asp Ter Ter His Lys Tyr Asp Val Ile Tyr Glu Gly Phe Ser
                965             970             975
                    M M         H A
                    A N         I L
                    E L         N U
                    2 1         3 1

TTT CAT CAA AAG CCC TTG TGT ATT TCT CTG TAA GCT T                 2965
Phe His Gln Lys Pro Leu Cys Ile Ser Leu Ter Ala Ser
            980             985
```

FIG. 5U

BACILLUS THURINGIENSIS STRAINS PRODUCING INSECTICIDALLY ACTIVE TOXINS

The present invention relates to novel bacterial genes, and to novel strains of the bacterium *Bacillus thuringiensis;* and to uses therefor.

The organism *Bacillus thuringiensis* produces a protein crystal endotoxin which kills insect larvae. It is not however toxic to mammals. It is thus very useful as an agricultural insecticide, in particular against Lepidoptera, Coleoptera and Diptera. Strains of *Bacillus thuringiensis* have been used as agricultural insecticides for a number of years.

The most extensively characterised strain of *Bacillus thuringiensis* active against coleopteran pests is *Bacillus thuringiensis* variety (var.) *tenebrionis*, as deposited in the German Collection of Microorganisms (Deutsche Sammlung von Microorganism) under the reference DSM 2803. We have now discovered novel strains of *Bacillus thuringiensis* having generally similar properties to DSM 2803, but distinguished therefrom by specific insecticidal activity against coleopteran larvae of the genus Diabrotica, as well as by toxicity to lepidopteran larvae. The novel properties of these strains appear to arise from novel genes that they contain.

According to the present invention we provide the novel strains JHCC 4835 and JHCC 4353 of *Bacillus thuringiensis,* deposited at the National Collections of Industrial and Marine Bacteria under the accession numbers NCIB 40091 and 40090, respectively.

We further provide novel δ-endotoxin genes capable of isolation from said strains JHCC 4835 and JHCC 4353. Such genes may be located either on the bacterial chromosome or on a plasmid. In a further aspect, out invention comprises recombinant DNA homologous with the DNA sequence set out in FIGS. 5A–5V hereof and coding for a novel insecticidally-active endotoxin of molecular weight about 81.2 kilodaltons (hereinafter referred to as "the 81 kD endotoxin"). In specific embodiments of our invention, recombinant DNA coding for insect endotoxins has been cloned from *Bacillus thuringiensis* JHCC 4835 into *E. coli* strains BL21/pJH11 and MC1022/pJH12, deposited at the National Collections of Industrial and Marine Bacteria under the accession numbers 40275 and 40278 respectively. The endotoxin gene in the latter deposit is lepidopteran-specific. We further provide recombinant DNA coding for a second lepidopteran-specific endotoxin gene derive from *Bacillus thuringiensis* strain JHCC 4835, which has been deposited in the form of a bacteriophage Lambda EMBL4 clone CL5 with the National Collections of Industrial and Marine Bacteria under the accession number 40279.

Recombinant DNA according to our invention may comprise genes of varying lengths encoding insecticidally-active proteins. When cloning DNA from the bacterial chromosome it is convenient to use bacteriophage Lambda vectors or other cloning vectors that sequester the recombinant DNA from host cell enzymes that might cause homologous recombination.

We further provide novel insecticidal compositions characterised in that they contain the δ-endotoxin produced by said strains JHCC 4835, JHCC 4353 and *E. coli* BL21/pJH11, and a method of protecting plants from insect attack which comprises exposing the larvae to a δ-endotoxin produced by the said strains JHCC 4353, JHCC 4835 and *E. coli* BL21/pJH11.

The strains JHCC 4835 and JHCC 4353 were soil isolates from Marshall, Iowa, USA and Dallas, Iowa, USA respectively. In colony morphology they are generally similar to DSM 2803, and to strain HD-1 which is insecticidal to lepidopteran larvae.

The morphology of the strains of the invention is compared with that of known strains in Table 1.

Biochemical properties of the new and the known strains are compared in Tables 2–4. It will be seen that there are may similarities between the strains.

In view of these biochemical similarities it is surprising that the gene encoding the 81 kD endotoxin in *E. coli* BL21/pJH11 shows very little DNA sequence homology to the *B. thuringiensis* var. *tenebrionis* endotoxin gene of DSM 2803. Use of the coding sequence for the *B. thuringiensis* var. *tenebrionis* endotoxin gene as a DNA probe under relatively mild stringency conditions (3× Standard Saline Citrate at 37° C. is not sufficient to generate a signal from the coding sequences for this endotoxin gene in strains JHCC 4835 and JHCC 4353.

Similarly, use of the coding sequence for the lepidopteran-specific CryIA(c) (this system of nomenclature is described by Höfte and Whitely in Microbiol. Reviews, 53, 1989 at pages 242–255) endotoxin gene from a *Bacillus thuringiensis* var. *kurstaki* strain is not sufficient to generate a DNA hybridisation signal from the coding sequence for the 81 kD endotoxin. Also, use of the novel gene coding sequence as a DNA probe does not generate a hybridisation signal from the *tenebrionis* gene or the three CryIA genes.

The newly-discovered *B. thuringiensis* strains JHCC 4853 and JHCC 4353 show a significantly different specificity of insecticidal activity as compared with DSM 2803. In particular, 4385 and 4353 show more selective activity against beetles than known coleopteran-active *B. thuringiensis* strains in that they are specifically larvacidal to *Diabrotica spp.* In addition, strains JHCC 4835 and JHCC 4353 are larvacidal to lepidopteran pests whereas strain DSM 2803 is not. On the molecular level, the newly discovered gene in *Bacillus thuringiensis* strains JHCC 4835 and 4353 encode a gene product which shows a significantly different spectrum of insecticidal activity as compared with the coleopteran-specific endotoxin gene in DSM 2803 or the lepidopteran-specific CryIA endotoxin genes in HD1 and other var. *kurstaki* strains.

The new endotoxin gene encodes an 81.2 kilodalton endotoxin that has a completely novel activity spectrum: it is toxic to both lepidopteran and coleopteran larvae. This is particularly surprising since the *Bacillus thuringiensis* strain from which it is derived is not toxic to all Coleoptera, but rather is Diabrotica-specific. Possible explanations for this finding may include: a low concentration of this protein in the crystal that the microorganism produces; inaccessibility of the protein in the crystal; presence of the toxin in the crystal as a protoxin which is not converted to the active form in the gut of certain insects; or other so far unrecognised factors.

The *Bacillus thuringiensis* strains according to the invention may be prepared in any quantity required by fermenting a sample of NCIB 40091 or 40090 obtained from the National Collections of Industrial and Marine Bacteria under suitable conditions in an appropriate medium. Such conditions and media are well known to the art. The media will, for example, generally contain a nitrogen source (eg fish protein) and a carbohydrate source such as starch. Suitable conditions include a temperature in the range 15°–45° C., and an approximately neutral pH. Fermentation may be conveniently carried out in batches, typically for period of 3–5 days.

*E. coli* strains carrying cloned endotoxin genes according to the invention may be prepared by growing cells to stationary phase on solid nutrient media (eg L agar) prior to scraping cell growth from the medium surface, lyophilising, and freezing before thawing and weighing out the insecticidal material.

Insecticidal compositions according to the invention may be obtained from the fermentation liquor by concentration, for example by centrifugation or filtration followed by addition of any desired and appropriate formulating agents. Formulating agents which may be useful include for example surface active agents, eg, wetting agent: solid diluents, dispersing agents and UV stabilisers. If desired, solid formulations may be prepared by known methods.

The process of the invention is generally carried out by treating (eg spraying) plants infested or liable to infestation by insects with insecticidal compositions as described above diluted with a diluent such as water. The insecticidal agent is the toxic δ-endotoxin: if desired this may be applied to the plants or insects infesting them independently of the bacteria that produce it. Separation of the crystalliferous protein from the bacteria *Bacillus thuringiensis*, or of the cloned gene product from the bacterium *E. coli*, is however generally not necessary.

Another method of carrying out the process of the invention is to arrange for the plant susceptible to insect attack to produce the δ-endotoxin in situ. This is done by cloning a δ-endotoxin gene from strain NCIB 40090 or NCIB 40091, by known means; providing it with a promoter sequence (for example the CaMV35S promoter) which will cause expression of the gene in plants; and transforming the plant by known methods. Suitable transformation methods may include the use of Ti plasmid vectors for Agrobacterium-mediated transformation of dicots, or direct DNA uptake methods such as embryo microinjection, or use of microprojectiles followed by protoplast regeneration. To obtain the greatest degree of expression of the gene the promoter sequence should be selected and engineered appropriately and other factors (for example codon usage) should be adapted to maximise expression in plants.

Coleopteran larvae which are combated by the process of the invention may be of various species. As noted above, the *Bacillus thuringiensis* strains of the invention kill only Diabrotica, including those shown in Table 5A below: while use of the insecticidal product from the cloned gene of our invention will kill other coleoptera as well.

TABLE 5A

| Common Name | Latin Name |
| --- | --- |
| Western Corn Rootworm | *Diabrotica virgifera virgifera* |
| Southern Corn Rootworm | *Diabrotica undecimpunctata howardi* |
| Northern Corn Rootworm | *Diabrotica barberi* |
| Mexican Corn Rootworm | *Diabrotica virgifera zea* |
| Banded Cucumber Beetle | *Diabrotica balteata* |
| Western Spotted Cucumber Beetle | *Diabrotica undecimpunctata undecimpunctata* |

Lepidopteran larvae which are combated by the process of the invention may include those listed in Table 5B.

TABLE 5B

| Tobacco budworm | *Heliothis virescens* |
| --- | --- |
| Corn earworm | *Heliothis zea* |
| European corn borer | *Ostrinia nubilalis* |
| Cabbage looper | *Trichoplusia ni* |
| Diamondback moth | *Plutella xylostella* |
| Fall army worm | *Spodoptera frugiperda* |
| Beet army worm | *Spodoptera exigua* |

The process of the invention may be used to protect a wide variety of plants prone to infestation by Coleoptera (Diabrotica if the *Bacillus thuringiensis* strains are used) or Lepidoptera. Specific examples of commercially important plants to be protected by the invention are maize (corn), tomatoes, potatoes, cotton, tobacco and cucurbits.

*Bacillus thuringiensis* JHCC 4835 and 4353 are var. *Kurstaki* strains according to tests with antibody to flagellar antigens. To date, var. *kurstaki* strains have been known only for their insecticidal effect on lepidopteran larvae. Surprisingly, these strains and indeed other *kurstaki* strains previously described by ICI (e.g. strain A20 deposited at the National Collections of Industrial and Marine Bacteria under accession number NCIB 12570 and the subject of our prior UK application no 8730132 filed 24 Dec. 1987) are active against coleopteran larvae of the genus Diabrotica, in additional to their expected activity against Lepidoptera. Moreover if the 81 kD endotoxin gene is used as a hybridisation probe, strongly hybridising sequences can be found in both chromosomal and plasmid DNA samples from other known *Bacillus thuringiensis* strains. These strains include var. *kurstaki* strains such as HD1, HD73 and HD241, and the var. *kenyae* strain HD123. In spite of this, the 81 kD endotoxin gene of the present invention has not been previously described, or recognised as being present in these or other *Bacillus thuringiensis* strains.

The invention may be further understood with reference to the accompanying drawings, in which:

FIGS. 5A–5V show the base sequence, the amino acid sequence, and the main restriction endonuclease recognition sites of the 81 kD endotoxin gene carried by pJH11;

Figure 1:
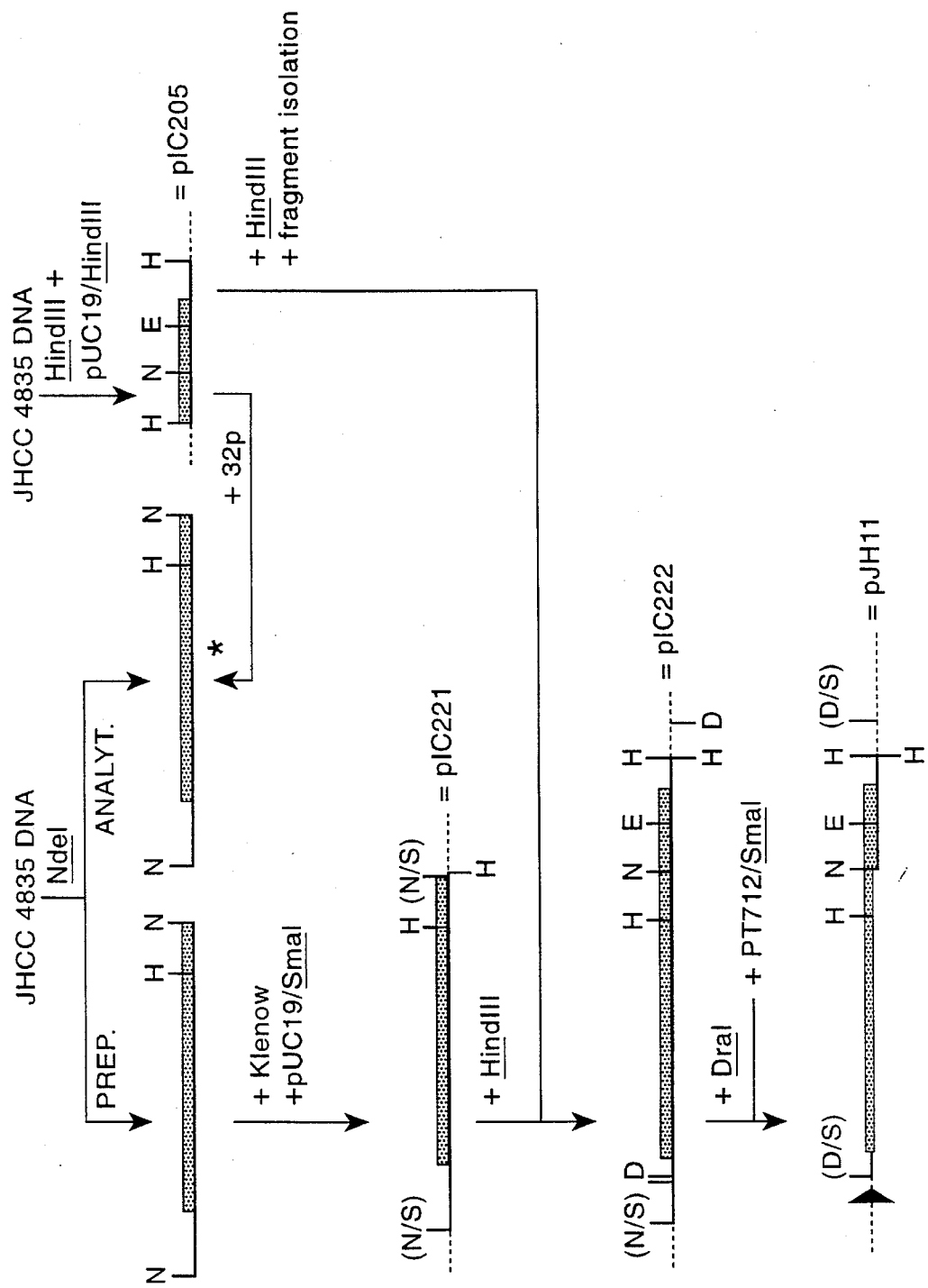
FIG. 1 shows diagrammatically the derivation of the cloned 81 kD endotoxin gene in the recombinant plasmid pJH11.

With further reference to FIG. 1, in this diagram, which is not drawn to scale, N represents restriction endonuclease NdeI, H=HindIII, E=EcoR1, D=DraI and S=SmaI. Restriction sites above the maps are in the cloned DNA, whereas sites below the maps are in the vector. Parentheses indicate sites rendered non-functional by "filling-in" with Klenow DNA polymerase. Dashed lines represent pUC19 vector DNA. Dotted liens represents PT712 vector DNA in clone pJH11 and the arrowhead represents the bacteriophage T7 promoter. The star represents a $^{32}$P-labelled DNA fragment.

Figure 2:
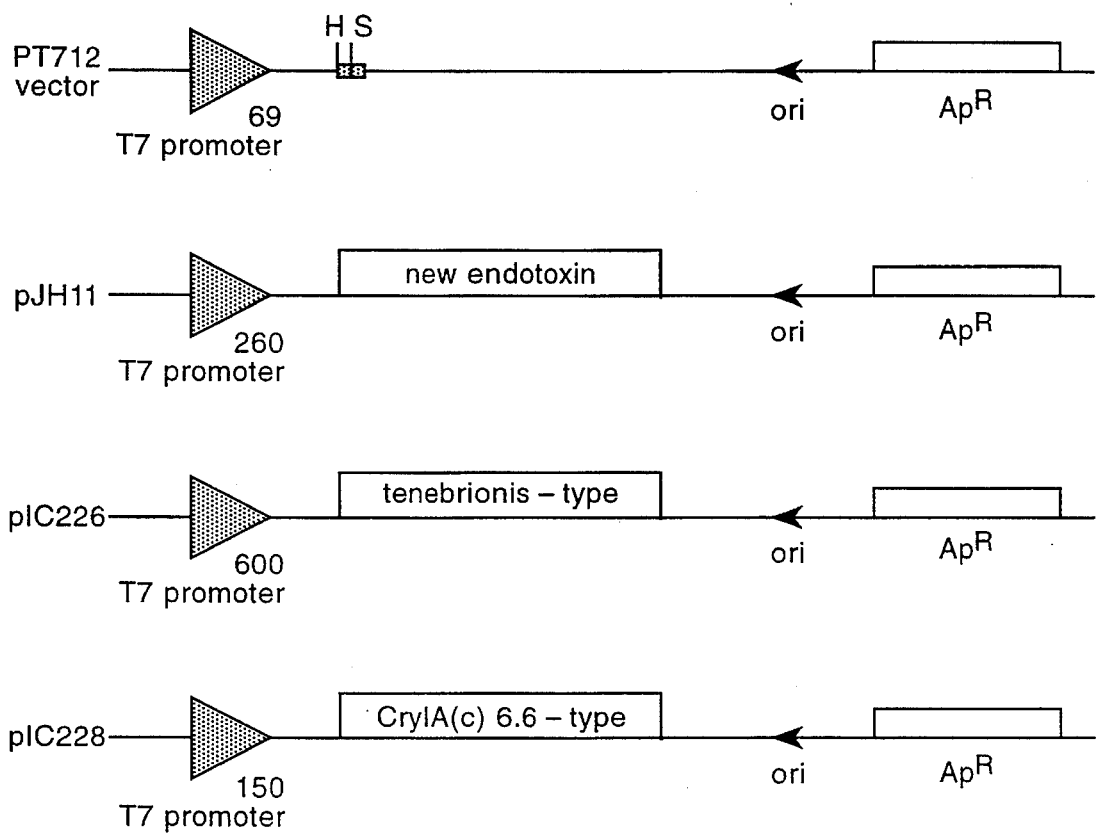
FIG. 2 shows diagrammatically the structure of pJH11, and the structures of the coleopteran-specific tenebrionis-type gene and the CryA 6.6-type gene cloned into the same vector system (PT712) and designated pIC 226 and pIC 228 respectively.

In FIG. 2, the figures below the maps represent the number of basepairs between the T7 RNA polymerase transcriptional start site and the beginning of the open reading frame. The large arrowhead represents the bacteriophage Y7 promoter. The solid block in PT712 represents the cloning site; H=HindIII and S=SmaI. Ap$^R$ indicates the gene encoding resistance to ampicillin.

Figure 3:
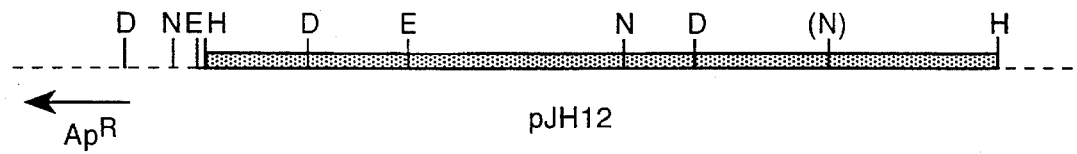
FIG. 3 shows diagrammatically the structure of the cloned lepidopteran-specific endotoxin gene in the recombinant plasmid pJH12.

In FIG. 3, the open box represents the cloned fragment which is about 7 kilobasepairs in length. The dashed lines indicate pUC19 vector DNA and Ap$^R$ is the gene encoding ampicillin resistance. The parentheses indicate an NdeI site which is only provisionally placed in the region shown; other restriction sites are represented by D=DraI, E=EcoR1, H=HindIII and N=NdeI.

Figure 4:
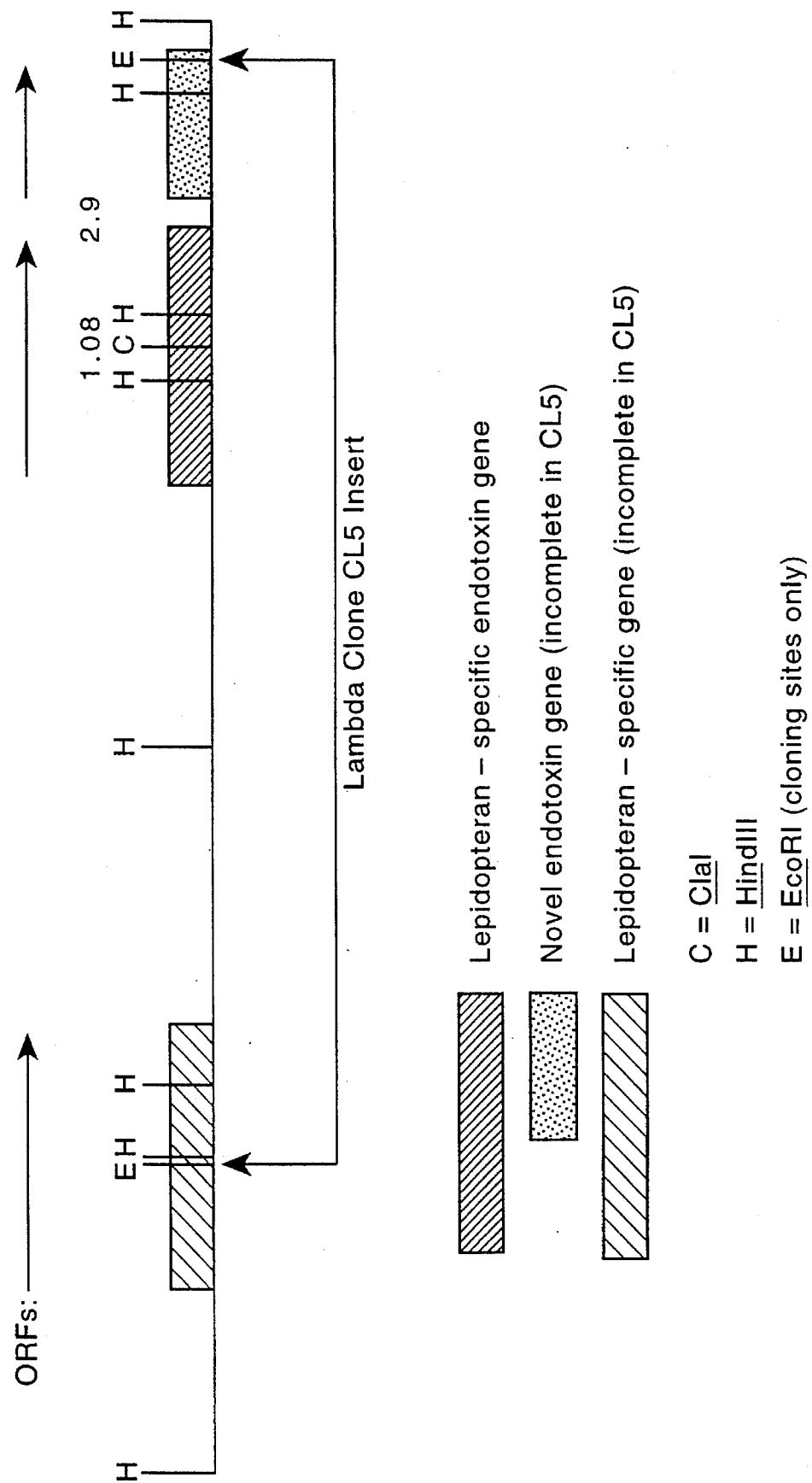
FIG. 4 shows diagrammatically the structure of the cloned lepidopteran-specific endotoxin gene in the recombinant lambda clone CL5.

With reference to FIG. 4, the only EcoR1 (E) sites shown are those at which the Lambda vector and the cloned insert fragment are joined. Open reading frames (ORFs) are shown by arrows above the map. The numbers above the map are the approximate fragment lengths of the selected HindIII fragments. The ClaI (c) site shown is not the only ClaI site in the insert. The diagram is not drawn to scale; the cloned insert fragment is approximately 16 kilobase pairs in length.

FIGS. 5A–5V show the base sequence, the amino-acid sequence and the main restriction sites of the gene encoding the 81 kD endotoxin protein and flanking DNA. The open reading frame begins at base number 355 and ends at base number 2514 with the G of the termination (Ter) codon TAG.

Figure 6:
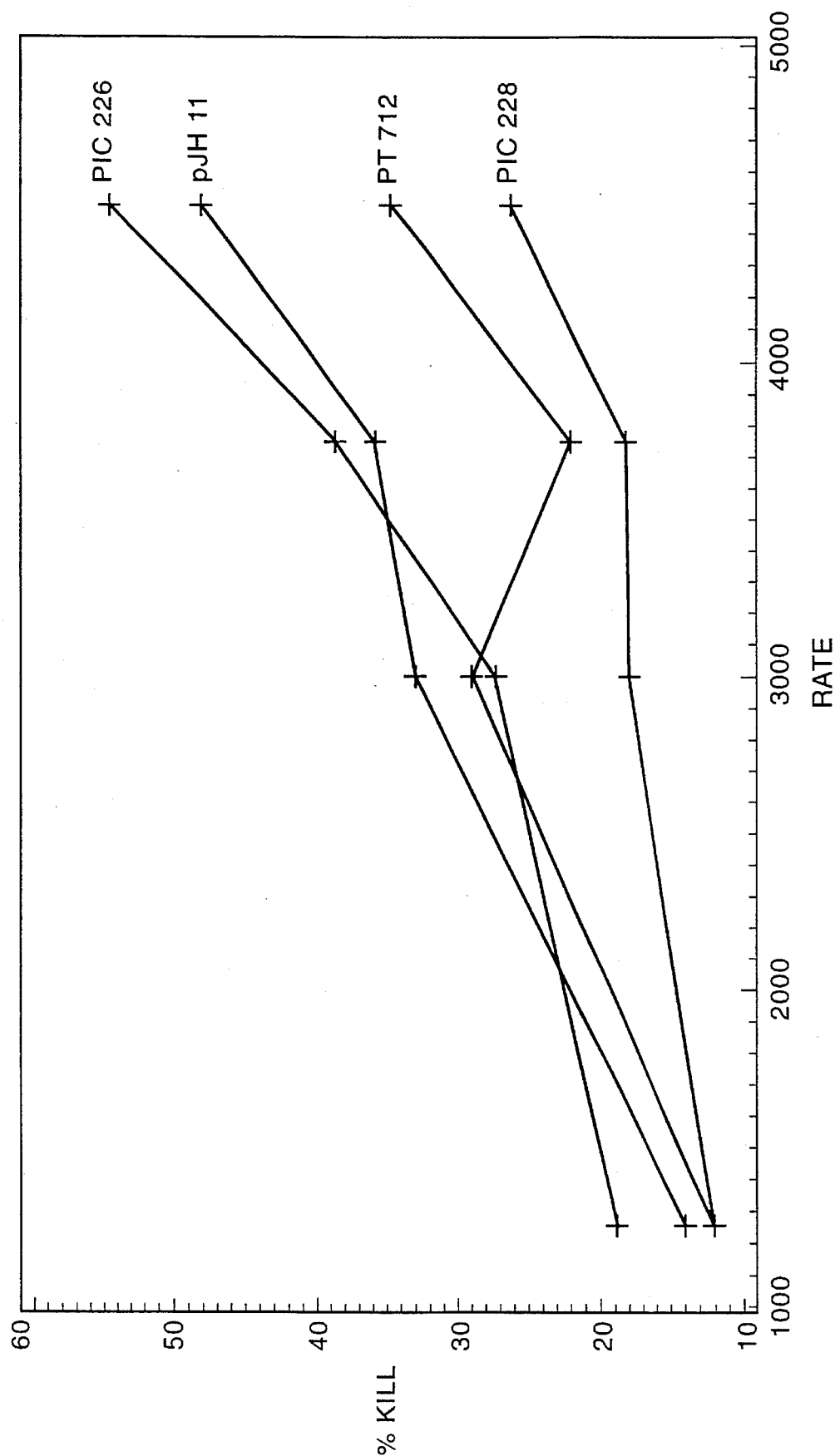
FIG. 6 shows graphically the mean values of 12 separate bioassays testing the efficacy of recombinant *E. coli* strain MC1022/pIC244 against first-instar larvae of Western Corn Rootworm at 4 days after treatment.

FIG. 6 is a graphical representation of the Western Corn Rootworm bioassay of cloned endotoxin gene products at 4 days after treatment (DAT). Points on the graph are mean values of percent mortality at a given rate.

Figure 7:
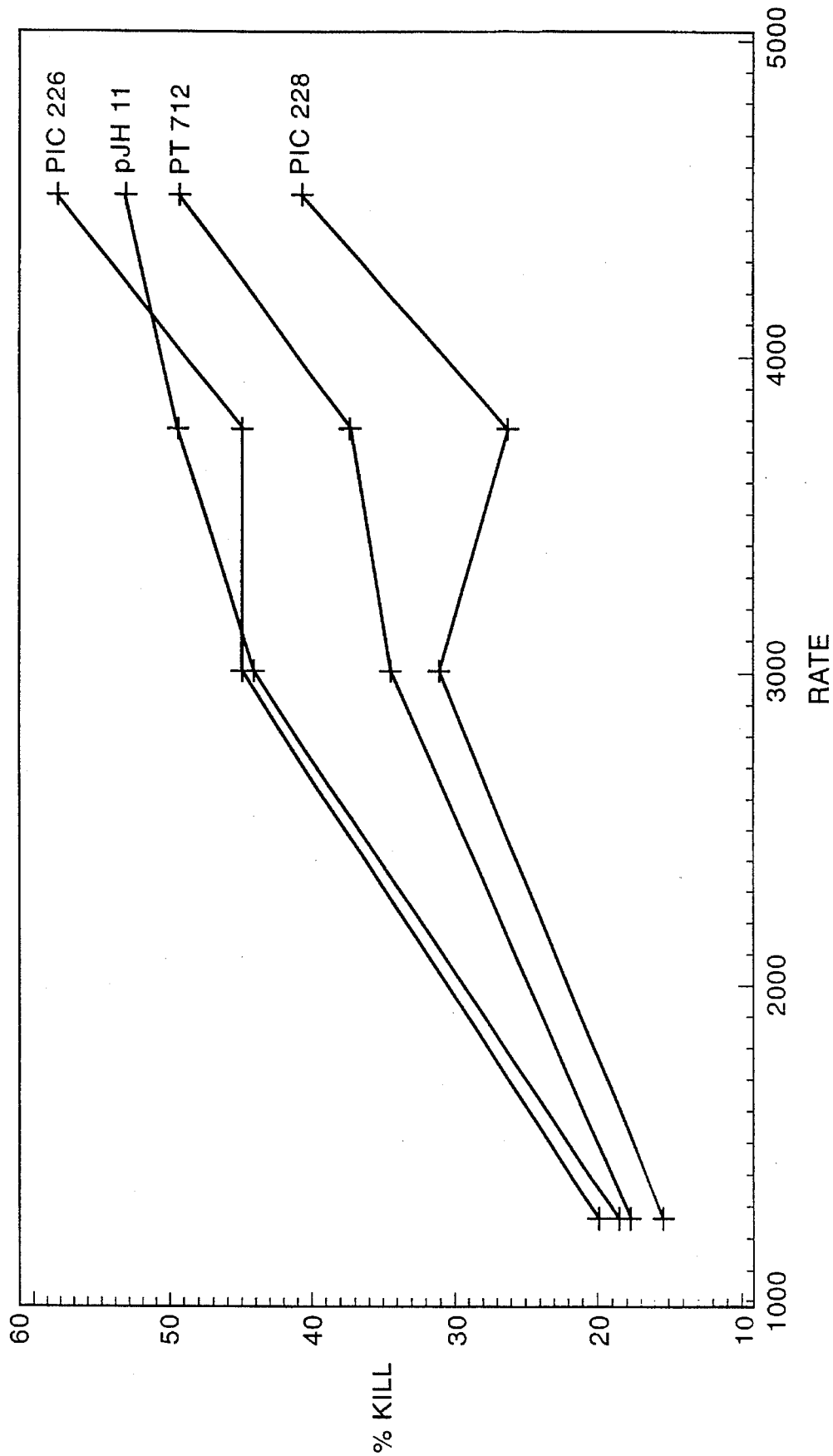
FIG. 7 shows graphically the mean values of 12 separate bioassays testing the efficacy of recombinant *E. coli* strain MC1022/pIC244 against first-instar larvae of Western Corn Rootworm at 5 days after treatment.

FIG. 7 is a graphical representation of the Western Corn Rootworm bioassay of cloned endotoxin gene products at 5 days after treatment (DAT). Points on the graph are means values of percent mortality at a given rate.

The following Examples illustrate the invention.

EXAMPLE 1

Isolation of the B. thuringiensis Strain JHCC 4835 According to the Invention Soil samples were diluted by placing 5.0 g of the sample into 45 ml of 0.5% peptone to give a $10^{-1}$ dilution prior to emulsification. The sample was then heated to 60° C. for 10 minutes in a water bath. Sequential dilutions were then made prior to plating 0.1 ml of the $10^{-3}$ and $10^{-5}$ dilutions onto B. cereus selective agar plates (Bacillus cereus agar base, Oxoid) and esculin agar plates (in g/liter of $H_2O$: esculin 1.0; ferric citrate 0.5; peptone 10; NaCl 5; Oxoid agar 10). The plated samples were incubated at 30° C. for 5 days. Slides were made of potential B. thuringiensis colonies, stained according to Smirnoff's procedure and examined microscopically at 1000× magnification for the presence of stained, parasporal crystals.

Crystal-positive colonies were streaked onto L agar (10 g tryptone, 10 g yeast extract, 5 g NaCl, 10 g agar per liter) in order to ensure a pure culture, and incubated at 30° C. Purified colonies were incubated overnight in L broth; after incubation an equal volume of 80% sterile glycerol was added prior to storage at −70° C.

The strain JHCC 4353 was extracted by a similar procedure.

EXAMPLE 2

Propagation of the B. thuringiensis Strains JHCC 4835 and JHCC 4353 on Solid Media Inoculum was transferred from a glycerol storage vial onto an L agar plate to check for purity. A representative sweep of colonies was then used to inoculate 5 ml of broth (10 g tryptone, 10 g yeast extract, 5 g NaCl per liter) prior to incubation with shaking at 30° C. for 3–5 hours. One milliliter of this culture was then used to inoculate a preparative (210 mm×210 mm) Petri plate containing 300 ml of CRL 1 medium agar (in g or ml/liter of water: nutrient both 8; glucose 6; yeast extract 5; xylose 0.5; cotton seed flour extract 30 ml; corn steep liquor 3.2 ml; May Mendel's salt mixture 1 ml; Oxoid agar 15). Mary Mendel's salt mixture is:

| Mary Mendel's Salts | |
| --- | --- |
| Distilled water | 495 ml |
| HCl conc. | 5 ml |
| FeSO$_4$ | 2.5 g |
| MnSO$_4$, H$_2$O or MnCl$_2$.4H$_2$O | 0.98 g |
| ZnCl$_2$ or ZnSO$_4$.4.H$_2$O | 1.76 g |

Cultures were incubated for 5 days at 30° C. The cells, spores and crystals were then harvested by scraping confluent growth from the agar surface prior to freeze-drying.

EXAMPLE 3

Propagation of the B. thuringiensis Strain JHCC 4835 and JHCC 4353 in Liquid Culture According to the Invention Inoculum was transferred from a glycerol storage vial to a 250 ml Erylenmeyer flask containing 100 ml of CRL 1 medium (in g or ml/liter of water: nutrient broth 8; glucose 6; yeast extract 5; xylose 0.5; cotton seed flour extract 30 ml; corn steep liquid 3.2 ml; Mary Mendel's salt mixture 1 ml) and incubated with agitation at 30° C. and 3400 rpm. After 24 hours, the entire 100 ml was used to inoculate 1 liter of the same medium in a 2 L flask; this was incubated with agitation for 5 days at 30° C. The cells, spores and crystals where then harvested by centrifugation and acetone precipitated using the Dulmage method.

EXAMPLE 4

Formulation According to the Invention

Upon completion of the fermentation cycle, JHCC 4353 or JHCC 4835 bacteria can be harvested by first separating the B. thuringiensis spores and crystals from the fermentation broth as described in Example 2. The recovered spores and crystals can be resuspended in 100 ml of water and formulated into a liquid concentrate by adding 4.9 g of Morwet D-425 (dispersing agent), 4.9 g of Veegum HV (suspending agent), 4.9 ml of Tween 80 (wetting agent) and 24.4 ml of Sorbo (anti-freezing agent). Each ingredient is added separately in order stated above. The product is kept at 4° C. prior to use.

EXAMPLE 5

Cloning of Plasmid-derived Endotoxin Genes from B. thuringiensis Strain 4835

Endotoxin genes are cloned from covalently closed circuit (ccc) plasmid DNA prepared from B. thurigiensis strain 4835 as follows:

A 500 ml culture of strain 4835 is grown in L broth at 37° C., with shaking, to an absorbance value at 600 mm of 1.00 optical density (O.D) units. Cells are harvested by centrifugation at 8000 revolutions per minute (rpm) for 10 minutes at 4° C., then re-suspended in 5 ml TE buffer (50 mm Tris HCl pH7.6, 20 mM EDTA). The resuspended cells are added to 95 ml TE buffer containing 1% sodium dodecyl sulphate (SDS) and 0.085M NaOH, pH12.4 lysin of the cell suspension occurs during a incubation at room temperature. 10 ml of 10% SDS are then added to the lysate; the solution is mixed gently prior to the gradual addition of 10 ml 2M Tris HCl pH7.0 with gentle mixing. 34 ml of 5M NaCl is added and the solution is mixed well prior to overnight incubation on ice-water. The lysate is centrifuged at 9000 rpm for 15 minutes at 4° C. and the supernatant carefully transferred to a new centrifuged bottle prior to the addition of 36 ml 50% polyethylene glycol (PEG) 600 in TE buffer. The lysate is incubated on ice-water for 3 hours (minimum) to overnight prior to centrifugation at 10,000 rpm for 10 minutes at 4° C. The pellet is dissolved in 9 ml TE buffer and 100 µl 5 mg/ml RNA (treated at 100° C. for 5 minutes, prior to use) and incubated at 45° C. for 10 minutes, prior to the addition of 9.23 g caesium chloride (CsCl). After the CsCl is dissolved, 0.9 ml of 5 mg/ml ethidium bromide is added prior to isopycnic centrifugation of the mixture at 40,000 rpm for 48 hours at 15° C., and isolation of the ccc DNA band. After removal of the CsCl and ethidium bromide by conventional techniques, high molecular weight plasmid ccc DNA (greater than 40 kilobase pairs) is isolated by size fractionation on 10%–40% sucrose step gradients prior to digestion with appropriate restriction endonucleases (ie, those which do not cleave the DNA in the endotoxin structural gene), ligation into appropriately digested plasmid cloning vectors (eg, pUC18 or pUC19), and transformation into an appropriate E. coli host strain (the specific strain used is MC1022, which is an ampicillin-sensitive strain of the genotype ara D139, Δ(ara, leu) 7697, Δ(lac Z) M15, gal U, gal K, str A. Transformants resistant to appropriate antibiotics which select for the introduced plasmid vector were then screened for recombinant endotoxin genes by standard DNA hybridisation methods, using as probes the cloned tenebrionis gene (plus flanking sequences) and a cloned CryIA gene.

EXAMPLE 6

Cloning of Chromosomal Endotoxin Genes from B. thuringiensis Strain 4835

Endotoxin genes were cloned from chromosomal DNA prepared from strain 4835 as follows:

A 500 ml culture of strain 4835 was grown in L-broth at 37° C., with shaking, to an Absorbance value at 600 nm of 1.00 optical density units. Cells were harvested by centrifugation at 8000 rounds per minute (rpm) for 10 minutes at 4° C., then re-suspended in 5 ml TES buffer (50 mM Tris-HCl pH7.5, 50 mM NaCl, 5 mM EDTA). Cells were treated for 30 minutes at 37° C. with lysosyme (0.5 mg/ml final concentration) and RNase (0.1 mg/ml final concentration taken form a stock solution of 5 mg/mol boiled at 100° C. for 5 minutes prior to use). Lysis was completed by the addition of Sarcosyl to give a final concentration of 8.0% and incubation at 37° C. for 60 minutes in the presence of Pronase (0.5 mg/ml final concentration taken from a stock solution of 5 mg/ml pre-incubated at 37° C. for 60 minutes prior to use). Lysate volume was adjusted to 9.0 ml in the 50 mM Tris-HCl pH 7.6, 10 mM EDTA, prior to the addition of 9.2 g caesium chloride (CsCl). After the CsCl dissolved, 1.25 ml of a 5 mg/ml solution of ethidium bromide was added prior to isopyonic centrifugation of the mixture at 40,000 rpm for 48 hours at 15° C.

After removal of CsCl and ethidium bromide by conventional techniques, an aliquot of purified chromosomal DNA was partially digested with the restriction endonuclease EcoR1 prior to ligation into EcoR1-digested bacteriophage λ EMBL4 vector DNA. Ligation reaction mixtures were packaged into viable phase particles using a commercially-available kit from Amersham International PLC.

The resultant recombinant phage particles were selected by growth on *E. coli* host strain PE392, a P2 lysogen of strain LE392 which has the genotype hsd R514 ($r_K^-$,$M_K^+$), sup E44, sup F58, lacY1 or Δ(lac12Y), gal K2, gal T22, met B1, trp R55. Recombinant phage carrying one or more endotoxin genes were detected by hybridisation of lysed plaques fixed to a duplicate set of nitrocellulose filter using as probes radiolabelled fragments of a CryIA-endotoxin gene and a 3'-terminal fragment of the gene for the 81 kD protein.

Plaques containing endotoxin genes were purified and characterised by restriction endonuclease mapping techniques well known in the art.

Chromosomal endotoxin genes can also be cloned directly into plasmid vectors (e.g. pUC19). This may necessitate cloning the gene in small fragments by the technique well known in the art as "chromosome walking". Problems with deletion events due to host-mediated homologous recombination can be circumvented by cloning in this manner and reconstructing the desired open reading frame by piecing the gene together after sequencing an appropriate number of overlapping gene fragments.

EXAMPLE 7

Solid Media Propagation of Insecticidally-active *E. coli* Strains Carrying Cloned Endotoxin Genes According to the Invention Inoculum was transferred from a glycerol storage vial to L agar Petri plates containing antibiotics suitable for selection of the cloning vector. Inoculated plates were incubated 24–72 hours to allow for the appearance of characteristic colonial morphology. A selection of single colonies of the correct appearance (e.g. rough colonies in the case of *E. coli* strain BL21/pJH11 carrying the cloned the 81 kD endotoxin gene) was used to inoculate a small volume of L broth [15 g Tryptone, 7.5 g yeast extract, 7.5 g NaCl per 1500 ml total volume] containing an antibiotic (e.g. ampicillin) suitable for selection for the plasmid vector carrying the cloned endotoxin gene. Cultures were grown to an an Absorbance value at 600 nm of 0.5–0.7 O.D. units. One milliliter (ml) of culture was used to inoculate, by spreading with a glass "spreader", a preparative (i.e. 245 mm×245 mm×20 mm) Petri plate containing L agar [L broth as above supplemented with 16 g Oxoid agar, an appropriate antibiotic and IPTG to a final concentration of 120 microgram/ml.]. Preparative plates were incubated overnight at 37° C. Bacterial growth was scraped from the preparative plates using a glass spreader. The scraped product, pooled from several plates if necessary, was transferred to a sterile plastic container and frozen for 2 hours at −20° C. prior to lyophilisation for 16–18 hours. The material was stored at −20 C. the dried product is crushed into an even powder prior to use as an insecticidal material in insect bioassays.

EXAMPLE 8

Purification of the novel 81.2 kilodalton endotoxin protein from the recombinant *E. coli* strain MC1022/pJH11. *E. coli* strain MC1022/pJH11 was prepared on solid media as described in Example 7, but the scraped cell mass was stored at −20 C. without lyophilisation. Frozen cells were thawed on ice prior to disruption by sonication at an amplitude of 14 microns for 9×20 seconds using a 1 cm diameter probe. The sonicated cells were then centrifuged at 9300×g at 4° C. to remove unbroken cells, prior to high-speed centrifugation (100,000×g for 60 minutes at 4° C.) to remove membranes. The high-speed extract was then subjected to ion-exchange chromatography over DEAE-Sepharose at pH 8.0. The column was then eluted with a 0–500 mM NaCl gradient, and fractions monitored by SDS-PAGE. Fractions containing the 81.2 kD protein were pooled, dialysed against 10 mM Tris pH8.0, and subjected to a second FPLC ion-exchange chromatography step, again eluting the bound proteins with a 0–500 mM NaCl gradient. Fractions containing the partially-purified 81.2 kD protein were identified and pooled prior to further purification by gel filtration chromatography. This process results in an endotoxin protein which is 90% pure and which may be used (with or without a concentration step) in insect bioassays.

Examples 9 and 10 illustrate the activity of the novel *B. thuringiensis* strains of the invention against different *Diabrotica spp.*

EXAMPLE 9

Efficacy of Larvacidal Activity of *B. thuringiensis* Strain JHCC 4835 against Western Corn Rootworm (*Diabrotica virgifera virgifera*)

For each *B. thuringiensis* strain, a mixture of spores and crystals was prepared by incubating the organism at 30° C. for 5 days on 210 mm×210 mm Petri plates as in Example 2, scraping confluent growth from the agar surface and freeze drying. For tests on first instar larvae of Western Corn Rootworm (*Diabrotica virgifera virgifera*), freeze dried spores and crystals were mixed sterile water and a sterile sucrose solution to give the treatment rates indicated in Table 7 in parts per million (ppm) and a final sucrose concentration of 2.5%. The solubilised spore crystal (treatment) mixture was homogeneously dispersed by sonication in a water bath sonicator for 5 minutes. The treatment was then vortexed and applied as 0.075 ml of solution to a disk 1.5 cm in diameter cut from "Teri towels" (Kimberly Clark product #34770). One test consisted of 5 Teri towel disks with applied treatment, each placed in a separate plastic Falcon Test dish prior to infestation with 5 first instar larvae per dish. Tests were placed in a closed styrofoam box with a moistened Teri towel as a humidity source; the box was incubated in a room held at 78° F.–80° F. for 3 more more days after treatment (DAT) prior to evaluation of the bioassay. The conditions inside the styrofoam box were 74° F.–76° F. and 80% relative humidity. Tests were evaluated using a dissecting microscope. The efficacy of these treatments at various concentrations (rates) is shown in Table 6.

EXAMPLE 10

Efficacy of Larvacidal Activity of *B. thuringiensis* Strain JHCC 4835 against Southern Corn Rootworm (*Diabrotica undecimpunctata howardi*)

For each *B. thuringiensis* strain, a mixture of spores and crystals were prepared by incubating the organism at 30° C. for 5 days on 210 mm×210 mm Petri plates as in Example 2, scraping confluent growth from the agar surface and freeze drying. Tests on first instar Southern Corn Rootworm (*Diabrotica undecimpunctata howardi*) were set up, incubated and evaluated as described in Example 9. The efficacy of these treatments at various concentrations (rates) is shown in Table 8.

EXAMPLE 11

Specificity of Insecticidal Activity of *B. thuringiensis* Strains JHCC 4835 and JHCC 4353

A mixture of spores and crystals was prepared by incubating the organism at 30° C. for 5 days on 210 mm×210 mm Petrie plates as in Example 2, scraping confluent growth from the agar surface and freeze-drying. Freeze-dried spores and crystals were mixed with a sterile 2.5% sucrose solution for tests on first-instar Souther Corn Rootworm (*Diabrotica undecimpunctata howardi*) larvae. Freeze-dried spores and crystals were mixed with sterile $H_2O$ and presented on potato leaves dipped in this suspension for tests on first-instar Colorado potato beetle (*Leptinotarsa decemlineata*) larvae. Freeze-dried spores and crystals were mixed with sterile $H_2O$ and presented on cotton cotyledons dipped in this suspension for tests on Boll Weevil (*Anthonomus grandis*) adults. The efficacy of these preparations at various concentrations in parts per million (ppm) is shown in Table 8. Comparison of the activity spectrum *B. thuringiensis* variety *tenebrionis* (DSM 2803) with those of strains JHCC 4835 and JHCC 4353 shows the more selective effect of the latter two strains (Table 8).

The efficacy of *B. thuringiensis* strain JHCC 4835 in the control of various lepidopteran larvae is illustrated in Examples 12–15.

EXAMPLE 12

Efficacy of *B. thuringiensis* Strain JHCC 4835 in the Control of Various Lepidopteran Larvae A mixture of spores and crystals was prepared as in Example 2, and mixed with an appropriate conventional artificial insect diet. Results are shown in Table 9 below. Comparison of the efficacy of *B. thuringiensis* variety *tenebrionis* (DSM 2803) with that of strain JHCC 4835 shows that only strain 4835, and the known var. *kurstaki* strain JHCC 4360, are insecticidal to lepidopteran larvae (Table 9).

EXAMPLE 13

Efficacy of *B. thuringiensis* Strain JHCC 4835 in the Control of Fall Army Worm (*Spodoptera frugiperda*)

A mixture of spores and crystals was prepared as in Example 2, and mixed with an appropriate conventional artificial insect diet. Results are shown in Table 10 below. Comparison of the efficacy of *B. thuringiensis* strain JHCC 4580 (an isolate very similar to var. *tenebrionis*) with that of strain JHCC 4835 shows that only strain 4835, and the known *kurstaki* strain JHCC 4360, are insecticidal to *S. frugiperda* (Table 10).

EXAMPLE 14

Efficacy of *Bacillus thuringiensis* Strains JHCC 4835 and 4353 in the Control of *Heliothis viriscens*

A mixture of spores and crystals was prepared as in Example 2, and mixed with an appropriate conventional artificial insect diet. Control of larvae obtained is shown in Table 11 below.

The efficacy and novel larvacidal activity spectrum of recombinant *E. coli* cells carrying the cloned endotoxin gene encoding the 81.2 kD protein are illustrated in Examples 15–17

EXAMPLE 15

Efficacy of the larvacidal activity of the 81 kD endotoxin expressed by recombinant *E. coli* strain MC1022/pJH11 in controlling European Corn Borer (*Ostrinia nubilalis*)

*E. coli* strain MC1022/pJH11 was prepared on solid media as described in Example 7. Freeze-dried cells were thawed and mixed with an appropriate conventional artificial insect diet to give the final treatment concentration in parts per million (ppm) shown in Table 12. Tests were infested with first instar European corn borer larvae and evaluated at 6 days after treatment (DAT). *E. coli* strains carrying the recombinant plasmid with the 81 kD endotoxin gene (pJH11) and those carrying the CryIA 6.6 type lepidopteran-specific gene (pIC228) were insecticidal, whereas those carrying the vector only (PT712) or the *tenebrionis*-type gene (pIC226) were not.

EXAMPLE 16

Efficacy of the larvacidal activity of the 81 kD endotoxin expressed by recombinant *E. coli* strain MC1022/pJH11 in controlling Colorado Potato Beetle (*Leptinotarsa decemlineata*).

*E. coli* strain MC1022/pJH11 was prepared on solid media as described in Example 7. Freeze-dried cells were thawed, mixed with sterile H2O and presented on potato leaves dipped in this suspension for tests on first-instar larvae of Colorado Potato Beetles (*Leptinotarsa decemlineata*) to give the final treatment concentration in parts per million (ppm) shown in Table 13. *E. coli* strains carrying the recombinant plasmid with the 81 kD endotoxin gene (pJH11) and those carrying the *tenebrionis*-type gene (pIC226) were insecticidal whereas those carrying the vector only (PT712) or the CryIA 6.6 type lepidopteran-specific gene (pIC228) were not.

EXAMPLE 17

Efficacy of the Larvacidal Activity of the 81 kD Endotoxin Expressed by Recombinant *E. coli* Strain MC1022/pJH11 in Controlling Western Corn Rootworms (*Diabrotica virgifera virgifera*)

*E. coli* strain MC1022/pJH11 was prepared on slid media as described in Example 7. For tests on first instar larvae of Western Corn Rootworm (*Diabrotica virgifera virgifera*), freeze dried cells were thawed, mixed with sterile water and a sterile sucrose solution to give the treatment rates indicated and a final sucrose concentration of 2.5%. The solubilised cell (treatment) mixture was homogeneously dispersed by sonication in a water bath sonicator for 5 minutes. The treatment was then vortexed and applied as 0.075 ml of solution to a disk 1.5 cm in diameter cut from "Teri towels" (Kimberly Clark product #34770) as described in Example 9 to give the final treatment concentration in parts per million (ppm) shown in Tables 14 & 15. These tests were read at 4 and 5 DAT and the results were subjected to statistical analysis. Results are presented graphically in FIGS. 6 & 7 and indicate that *E. coli* strains carrying the recombinant plasmid with the 81 kD endotoxin gene (pJH11) and those carrying the *tenebrionis*-type gene (pIC226) were insecticidal whereas those carrying the vector only (PT712) of the CryIA 6.6 type lepidopteran-specific gene (pIC228) were not; the differences in activity between these two groups of strains (pJH11 and pIC226 versus the vector PT712 and pIC228) are statistically significant.

The efficacy and novel larvacidal activity spectrum of the partially-purified and purified novel 81.2 kD endotoxin protein are illustrated in Examples 18–20.

EXAMPLE 18

Efficacy of the Larvacidal Activity of the Partially-purified and purified 81 kD Endotoxin in Controlling European Corn Borer (*Ostrinia nubilalis*)

Partially-purified and purified 81 kD endotoxin protein was prepared from freeze-dried recombinant *E. coli* cells MC1022/pJH11 as described in Example 8. Fractions from the second FPLC ion-exchange column were designated MonoQ A, B, and C and contained about 50%, 50%, and 25% 81.2 kD endotoxin protein respectively. These fractions were added to conventional artificial insect diet to give the treatment rates in ppm shown in Table 16 in bioassays to test insecticidal activity on first-instar larvae of European corn borer (*Ostrinia nubilalis*). The results in Table 19 show that all fractions were active in producing either mortality or stunting of larval growth. Purified 81.2 kD protein was also tested and found to be insecticidal to European corn borer larvae and to stunt larval growth (Table 17).

EXAMPLE 19

Efficacy of the larvacidal activity of the partially-purified and purified 81 kD endotoxin in controlling Colorado Potato Beetle (*Leptinotarsa decemlineata*).

Partially-purified and purified 81.2 kD endotoxin protein was prepared from freeze-dried recombinant *E. coli* cells MC1022//pJH11 as described in Example 8. Fractions from the second, FPLC ion-exchange column were designated MonoQ A, B, and C and contained about 50%, 50% and 25% 81.2 kD endotoxin protein respectively. These fractions and the purified 81.2 kD protein were mixed with sterile H2O and presented on potato leaves dipped in this suspension for tests on first-instar larvae of Colorado Potato Beetles (*Leptinotarsa decemlineata*) to give the final treatment concentration in parts per million (ppm) shown in Table 18. The results in Table 18 show that all fractions ere insecticidal to Colorado Potato Beetle larvae.

EXAMPLE 20

Efficacy of the larvacidal activity of the partially-purified and purified 81 kD endotoxin in controlling Western Corn Rootworms (*Diabrotica virgifera* virgifera).

Partially-purified and purified 81 kD novel endotoxin protein was prepared from freeze=dried recombinant *E. coli* cells MC1022/pJH11 as described in Example 8. Fractions from the second, FPLC ion-exchange column were designated MonoQ, A, B, and C and contained about 50%, 50%. and 25% 81.2 kD endotoxin protein respectively. These fractions and the purified 81.2 kD protein were mixed with sterile water and a sterile sucrose solution to give the treatment rates indicated in Table 19, and a final sucrose concentration of 2.5%. Tests on first-instar larvae of Western Corn Rootworm were carried out as described in Example 18. The results in Table 19 indicate that the 81.2 kD endotoxin is insecticidal to Western Corn Rootworm larvae.

The following microorganisms and clones referred to in the specification have been deposited at the National Collections of Industrial and Marine Bacteria, 23 St. Machar Drive, Aberdeen AB 2 1RY, Scotland:

| Name | Deposit Number | Date |
|---|---|---|
| *Bacillus thuringiensis* | | |
| A20 | 12570 | 20 October 1987 |
| JHCC 4835 | 40091 | 7 December 1988 |
| JHCC 4353 | 40090 | 7 December 1988 |
| *E.coli* | | |
| BL21/pJH11 | 40275 | 6 April 1990 |
| MC1022/pJH12 | 40278 | 24 April 1990 |
| Bacteriophage Lambda EMBL4 clone CL5 | 40279 | 26 April 1990 |

TABLE 1

MORPHOLOGY

| Strain | Crystals | Cell Morphology | Colony Morphology (Cultured on Bacillus Cereus selective Agar) |
|---|---|---|---|
| HD-1 | Medium bipyramids plus undefined shaped crystals | Rods with terminal spores which do not distend the cell | Large colonies, yellow centers. Egg yolk lecithinase: NEGATIVE |
| DMS 2803 | Small irregular crystals; few bipyrimidal crystals | Rods with terminal spores which do not distend the cell | Large Colonies, blue centers. Egg yolk lecithinase: NEGATIVE |
| JHCC 4353 | Large, mainly regular bipyrimidal crystals | Rods with oval, terminal or sub-terminal spores which do not distend the cell | Large blue colonies with yellow centers. Egg yolk lecithinase: POSITIVE |
| JHCC 4835 | Large, mainly regular bipyrimidal crystals | Rods with oval, terminal or sub-terminal spores which do not distend the cell | Large blue colonies with yellow centers. Egg yolk lecithinase: POSITIVE |

TABLE 2

Biochemical Markers on Microtitre Plate

| Reagent | HD-1 | DSM 2803 | JHCC 4353 | JHCC 4835 |
|---|---|---|---|---|
| Glycerol | − | − | − | − |
| Erythritol | − | − | − | − |
| D-arabinose | − | − | − | − |
| L-arabinose | − | − | − | − |
| Ribose | + | +/− | + | + |
| D-xylose | − | − | − | − |
| L-xylose | − | − | − | − |
| Adonitol | − | − | − | − |
| β-methyl-xyloside | − | − | − | − |
| Galactose | − | − | − | − |
| D-glucose | + | + | + | + |
| D-fructose | + | + | + | + |
| D-mannose | − | + | − | − |
| L-sorbose | − | − | − | − |
| Rhamnose | − | − | − | − |
| Dulcitol | − | − | − | − |
| Inositol | − | − | − | − |
| Mannitol | − | − | − | − |
| Sorbitol | − | − | − | − |
| α-methyl-D-mannoside | − | − | − | − |
| α-methyl-D-glucoside | − | − | − | − |
| N acetyl glucosamine | + | + | + | + |
| Amygdaline | − | − | − | − |
| Arbutine | + | + | + | + |
| Esculine | + | +/− | + | + |
| Salicine | + | − | + | + |
| Cellobiose | + | − | + | + |
| Maltose | + | + | + | + |
| Lactose | − | − | − | − |
| Melibiose | − | − | − | − |
| Saccharose | − | + | − | − |
| Trehalose | + | + | + | + |
| Inuline | − | − | − | − |
| Melezitose | − | − | − | − |
| D-raffinose | − | − | − | − |
| Amidon | + | + | + | + |
| Glycogene | + | + | + | + |
| Xylitol | − | − | − | − |
| β-gentiobiose | − | − | − | − |
| D-turanose | − | − | − | − |
| D-lyxose | − | − | − | − |
| D-tagatose | − | − | − | − |
| D-fucose | − | − | − | − |
| L-fucose | − | − | − | − |
| D-arabitol | − | − | − | − |
| L-arabitol | − | − | − | − |
| Gluconate | − | − | − | − |
| 2-ceto-gluconate | − | − | − | − |
| 5-ceto-gluconate | − | − | − | − |
| Ortho-nitro-phenyl galactoside (ONPG) | − | − | − | − |
| Arginine (ADC-arginine dihydrolase) | + | + | + | + |
| Lysine (LDH-lysine Decarboxylase) | + | − | − | − |
| Sodium Citrate (citrate utilisation) | − | + | + | + |
| Sodium Thiosulphate (H$_2$S production) | − | − | − | − |
| Urea (urease) | + | − | + | + |
| Tryptophane (deaminase detection) | − | − | − | − |
| Tryptophane (indole production) | − | − | − | − |
| Sodium Pyruvate (VP) | + | + | + | + |
| Gelatine (Gelatinase) | + | + | + | + |
| NO$_3$—NO$_2$ Reduction | + | − | + | + |
| Ornithine decarboxylase (ODC) | − | − | − | − |

+ = Positive Reaction
− = Negative Reaction
+/− = Weak Reaction

TABLE 3

Biochemical Markers on ID-IDENT Plates

| Reagent | HD-1 | DSH 2803 | JHCC 4353 | JHCC 4835 |
|---|---|---|---|---|
| 2-naphthyl-phosphate | − | − | − | − |
| 2-naphthyl-butyrate | + | + | + | + |
| 2-naphthyl-caprylate | + | + | + | + |
| 2-naphthyl-myristate | + | + | + | + |
| L-leucyl-2-naphthylamide | + | + | + | + |
| L-valyl-2-naphthylamide | + | + | + | + |
| L-cystyl-2- | + | + | + | + |

TABLE 3-continued

Biochemical Markers on ID-IDENT Plates

| Reagent | HD-1 | DSH 2803 | JHCC 4353 | JHCC 4835 |
|---|---|---|---|---|
| naphthylamide | | | | |
| N-benzoyl-DL-arginine-2-naphthylamide | 0 | + | + | + |
| N-glutaryl-phenylalanine-2-naphthylamine | 0 | + | + | + |
| 2-naphthyl-phosphate | + | + | + | + |
| naphthol-AS-B1-phosphate | + | + | + | + |
| 6-bromo-2-naphthyl-αD-galactopyranoside | − | − | − | − |
| 2-naphthyl-βD-galactopyranoside | − | − | − | − |
| Naphtol-AS-B1-βD glucuronide | − | − | − | − |
| 2-naphthyl-αD-glucopyranoside | + | + | + | + |
| 6-bromo-2-naphthyl-βD-glucopyranoside | + | − | − | + |
| 1-naphthyl-N-acetyl-βD-glucosaminide | − | − | − | − |
| 6-Bromo-2-naphthyl-αD-mannopyranoside | − | − | − | − |
| 2-naphthyl-αL-fucopyranoside | − | − | − | − |

ID-IDENT is a Trade Mark of APT Analytab Products

TABLE 7

| | | *Diabrotica virgifera virgifera* % Mortality at 3 days after treatment | |
|---|---|---|---|
| Expt No | B. thuringiensis | Test Larvae* | Untreated Controls* |
| 1 | 4835 | 88 | 4 |
| | 4353 | 72 | 16 |
| 2 | 4835 | 50 | 4 |
| | 4353 | 60 | 8 |

*25 first-instar larvae per test group

TABLE 8

| | Southern Corn Rootworm | | Boll Weevil | Colorado Potato Beetle |
|---|---|---|---|---|
| Bt Strain | 3 DAT 4800 ppm | 6 DAT | 3 DAT 1200 ppm | 3 DAT 200 ppm |
| DSM 2803 tenebrionis | 8 | 92 | 87 | 100 |
| 4835 | 38 | 92 | 13 | 7 |
| 4353 | 12 | 68 | 13 | 0 |
| Control | 0 | 4 | 20 | 0 |

RESULTS = % MORTALITY
DAT = DAYS AFTER TREATMENT

TABLE 4

SENSITIVITIES TO ANTIBIOTICS

| Strain | C | CT | F | SF | NA | AMP | S | TET | OA | K | VA | RIF | LI | CN | CR | CAR | R |
|---|---|---|---|---|---|---|---|---|---|---|---|---|---|---|---|---|---|
| HD-1 | S | R | S | S | S | R | S | S | S | S | S | S | S | S | S | S | S |
| DSM 2803 | S | R | S | R | S | R | S | S | S | R | S | S/R | S | S | S | R | S |
| JHCC 4353 | S | R | S | S | S | R | S | S | S | S | S | S | S | S | S | R | S |
| JHCC 4835 | S | R | S | S | S | R | S | S | S | S | S | S | S | S | S | R | S |

S = SENSITIVE  R = RESISTANT  S/R = REDUCED SENSITIVITY
C = Chlorampheicol 50 ug/ml        CT = Colistin Sulphate 10 ug/ml
F = Nitrofuration 200 ug/ml         SF = Sulphfurazole 500 ug/ml
NA = Naladixic Acid 30 ug/ml        AMP = Ampicillin 25 ug/ml
S = Streptomycin 25 ug/ml           CR = Cephaloridine 25 ug/ml
TET = Tetracycline 50 ug/ml         K = Kanamycin 30 ug/ml
VA = Vancomycin 30 ug/ml            RIF = Rifampicin 2 ug/ml
OA = Oxolinic Acid 2 ug/ml          LI = Lincomycin 15 ug/ml
CN = Gentamicin 10 ug/ml            CAR = Carbenicillin 100 ug/ml
E = Erythromycin 10 ug/ml

TABLE 6

| | | % Mortality | | | | |
|---|---|---|---|---|---|---|
| | | SCRW | | CPB | | BW |
| Strain | ppm | 3 DAT | 6 Dat | ppm | 3 DAT | pm | 3 DAT |
| DSH 2803 | 4800 | 8 | 92 | 200 | 100 | 1200 | 87 |
| JHCC 4835 | 4800 | 38 | 92 | 200 | 7 | 1200 | 13 |
| JHCC 4353 | 4800 | 12 | 68 | 200 | 0 | 1200 | 13 |
| UNTREATED CONTROL | — | 0 | 4 | — | 0 | — | 20 | ppm = Parts per million
SCRW = Southern Corn Rootworm
CPB = Colorado Potato Beetle
BW = Boll Weevil
(RF) = % Reduction Feeding

TABLE 9

| Bt Strain | Rate (ppm) | H. zea | T. ni | P. xylostella |
|---|---|---|---|---|
| 4360 kurstaki | 5 | 85 | 95 | 100 |
| 4835 | 25 | 100 | 100 | 100 |
|  | 250 | 100 | — | — |
| 4580 tenebrionis type | 25 | 0 | 0 | 0 |
|  | 250 | 5 | — | — |
| Control | — | 0 | 0 | 10 |

RESULTS = % MORTALITY AT 4 DAYS AFTER TREATMENT

TABLE 10

Bt STRAINS VERSUS *Spodoptera Frugiperda* AT 6 DAYS AFTER TREATMENT

|  | 4580 tenebrionis | 4835 | 4360 kurstaki | Control |
|---|---|---|---|---|
| PREP 1 | 0 | 92 | 84 | 3 |
| PREP 2 | 0 | 60 | 80 | 3 |
| PREP 3 | 0 | 92 | 88 | 3 |
| PREP 4 | 8 | 100 | 100 | 3 |

RESULTS EXPRESSED AS % MORTALITY AT 80 PARTS PER MILLION

TABLE 11

B.t. STRAINS VERSUS *Heliothis virescens* AT 6 DAYS AFTER TREATMENT

|  | 4580 tenebrionis | | 4835 | | 4360 kurstaki | |
|---|---|---|---|---|---|---|
|  | 1 | 2 | 1 | 2 | 1 | 2 |
| PREP 1 | 4 | 8 | 100 | 96 | 100 | 100 |
| PREP 2 | 4 | 0 | 60 | 34 | 96 | 100 |
| PREP 3 | 9 | 0 | 100 | 100 | 100 | 100 |
| PREP 4 | 0 | 4 | 100 | 100 | 100 | 100 |

CONTROL 1 = 3.5%
CONTROL 2 = 2%
RESULTS EXPRESSED AS % MORTALITY AT 80 PARTS PER MILLION

TABLE 12

EUROPEAN CORN BORER BIOASSAYS

1ST Experiments

| Rate/% R.S. | | 1 | 2 | 5 | 6 | 7 | 8 |
|---|---|---|---|---|---|---|---|
| pIC228 | 500 ppm | 30 | 30 | 63 | 5 | 10 | 75 |
|  | % R.S. | 100 | 100 | 100 | 100 | 100 | 100 |
| pJH11 | 500 ppm | 15 | 75 | 85 | 72 | 85 | 80 |
|  | % R.S. | 100 | 100 | 100 | 100 | 100 | 100 |
| pIC226 | 500 ppm | 0 | 0 | 10 | 5 | 0 | 10 |
|  | % R.S. | 0 | 0 | 11 | 6 | 0 | 0 |
| PT712 | 500 ppm | 0 | 0 | 10 | 0 | 0 | 0 |
|  | % R.S. | 0 | 0 | 17 | 5 | 0 | 0 |
| Control |  | 0 | 0 | 8 | 3 | 0 | 8 |
|  | % R.S. | 0 | 3 | 11 | 0 | 0 | 3 |
| 4835F2 | 10 ppm | — | — | 100 | 90 | 80 | 100 |
|  | % R.S. | — | — | xxx | 100 | 100 | xxx |

RESULTS = % MORTALITY AT 6 DAT
% R.S. = % SURVIVORS OF REDUCED SIZE

TABLE 13

COLORADO POTATO BEETLE BIOASSAYS

| SAMPLE | RATE | PREP NUMBER | | | | | |
|---|---|---|---|---|---|---|---|
|  |  | 1 | 2 | 5 | 6 | 7 | 8 |
| pIC226 | 5000 ppm | 84 | 84 | 60 | 53 | 27 | 93 |
| pJH11 | 5000 ppm | 84 | 100 | 60 | 93 | 79 | 87 |
| PT712 | 5000 ppm | 0 | 17 | 7 | 14 | 7 | 14 |
| pIC228 | 5000 ppm | 0 | 4 | 13 | 7 | 0 | 23 |
| Control | — | 0 | 0 | 7 | 7 | 0 | 13 |
| 4580F2 | 40 ppm | — | — | 100 | 93 | 100 | 73 |

RESULTS = % MORTALITY AT 3 DAYS AFTER TREATMENT

TABLE 14

WESTERN CORN ROOTWORM BIOASSAY

| E. coli Recombinant Plasmid | Rate (ppm) | Prep-Experiment | | | | | | | |
|---|---|---|---|---|---|---|---|---|---|
|  |  | 5-1 | 5-2 | 6-1 | 6-2 | 7-1 | 7-2 | 8-1 | 8-2 |
| pIC226 (*tenebrionis*-type gene) | 4500 | 75 | 60 | 37 | 59 | 36 | 58 | 42 | 68 |
|  | 3750 | 36 | 40 | 36 | 56 | 40 | 28 | 64 | 64 |
|  | 3000 | 20 | 12 | 20 | 36 | 21 | 20 | 68 | 12 |
|  | 1250 | — | 28 | 12 | 16 | 20 | 48 | 20 | 19 |
| pJH11 (novel gene) | 4500 | 16 | 52 | 60 | 56 | 36 | 44 | 64 | 58 |
|  | 3750 | 28 | 36 | 42 | 13 | 46 | 40 | 68 | 48 |
|  | 3000 | 08 | 12 | 36 | 46 | 52 | 44 | 36 | 29 |
|  | 1250 | — | 12 | 20 | 04 | 40 | 0 | 16 | 28 |
| pIC228 (Cry IA lepidoteran-specific gene) | 4500 | 16 | 36 | 36 | 04 | 32 | 36 | 21 | 32 |
|  | 3750 | 20 | 24 | 17 | 13 | 20 | 40 | 12 | 27 |
|  | 3000 | 0 | 08 | 08 | 20 | 20 | 40 | 08 | 38 |
|  | 1250 | — | 08 | 11 | 24 | 20 | 24 | 0 | 17 |
| PT712 (vector only) | 4500 | 18 | 24 | 40 | 24 | 52 | 14 | 42 | 64 |
|  | 3750 | 08 | 28 | 36 | 40 | 32 | 24 | 12 | 28 |
|  | 3000 | 12 | 36 | 12 | 32 | 36 | 28 | 48 | 28 |
|  | 1250 | — | 12 | 12 | 16 | 24 | 04 | 20 | 16 |

RESULTS = % MORTALITY AT 4 DAYS AFTER TREATMENT

TABLE 15

WESTERN CORN ROOTWORM BIOASSAY

| E. coli Recombinant Plasmid | Rate (ppm) | Prep-Experiment | | | | | | | |
|---|---|---|---|---|---|---|---|---|---|
|  |  | 5-1 | 5-2 | 6-1 | 6-2 | 7-1 | 7-2 | 8-1 | 8-2 |
| pIC226 (*tenebrionis*-type gene) | 4500 | 92 | 72 | 70 | 62 | 72 | 92 | 75 | 79 |
|  | 3750 | 52 | 63 | 76 | 64 | 64 | 56 | 91 | 84 |
|  | 3000 | 68 | 44 | 56 | 40 | 36 | 48 | 100 | 44 |
|  | 1250 | — | 28 | 20 | 28 | 44 | 56 | 37 | 29 |
| pJH11 (novel gene) | 4500 | 56 | 56 | 88 | 68 | 68 | 76 | 84 | 67 |
|  | 3750 | 52 | 72 | 92 | 28 | 73 | 88 | 92 | 75 |
|  | 3000 | 12 | 40 | 79 | 56 | 77 | 64 | 60 | 68 |
|  | 1250 | — | 32 | 24 | 20 | 52 | 04 | 32 | 24 |
| pIC228 (Cry IA lepidopteran specific gene) | 4500 | 27 | 60 | 64 | 44 | 64 | 54 | 54 | 54 |
|  | 3750 | 32 | 40 | 25 | 52 | 32 | 48 | 29 | 50 |
|  | 3000 | 04 | 44 | 36 | 60 | 44 | 44 | 07 | 72 |
|  | 1250 | — | 24 | 15 | 40 | 20 | 40 | 07 | 29 |
| PT712 (vector only) | 4500 | 40 | 36 | 76 | 40 | 68 | 68 | 79 | 96 |
|  | 3750 | 40 | 56 | 60 | 44 | 56 | 52 | 50 | 72 |
|  | 3000 | 24 | 52 | 40 | 40 | 42 | 36 | 64 | 56 |
|  | 1250 | — | 20 | 13 | 32 | 36 | 13 | 41 | 24 |

RESULTS = % MORTALITY AT 5 DAYS AFTER TREATMENT

TABLE 16

EUROPEAN CORN BORER BIOASSAY AT 6 DAYS AFTER TREATMENT

| Rate (ppm) | NON-TREATMENT CONTROLS | | | (% MORTALITY/ AVE. SIZE IN mm) MonoQ Fractions | | | B.t. STRAIN |
|---|---|---|---|---|---|---|---|
| | Prep | Pre | Post | A | B | C | 4835 |
| 115 | 1 | — | — | 88/1.5 | | | |
| 98 | 2 | | | | | 56/1.75 | |
| 67 | 1 | | | | | 66/1.5 | |
| 65 | 2 | | | | | 67/1.8 | |
| 65 | 3 | | | | | 78/1.5 | |
| 62 | 1 | | | | 100/1.1 | | |
| 57 | 2 | | | | 71/2.0 | | |
| 42 | 2 | | | 89/1.5 | | | |
| 11.5 | 3 | | | | | | 78/1.75 |
| 10 | 2 | | | | | | 62/1.8 |
| 6.5 | 2 | | | | | 17/2.7 | |
| 6.5 | 3 | | | | | 22/3.1 | |
| 6.3 | 1 | | | | 22/2.7 | | |
| 6.0 | 2 | | | | 20/2.5 | | |
| 4 | 2 | | | 0/2.4 | | | |
| 3.8 | 1 | | | 11/5.4 | | | |
| 3 | 1 | | | | | 0/5.0 | |
| — | 1 | 0/8.5 | 0/10 | | | | |
| — | 2 | 11/6.2 | 0/6.0 | | | | |
| — | 3 | 0/9.5 | 13/9.1 | | | | |

AVE SIZE IN mm = Average Size Of Surviving Larvae

TABLE 17

81kD PROTEIN VS. EUROPEAN CORN BORER

| | | IA | | JH | |
|---|---|---|---|---|---|
| | | Rate | % Mortality | % Mortality | Ave. Size |
| PREP 1 | | | | | |
| 81kD | Prot | 83 ppm | — | 0 | 2.7 mm |
| 17/20 | Ctrl | 5 ppm | — | 0 | 9.5 mm |
| Tris | Ctrl | — | — | 0 | 10 mm |
| PREP 2 | | | | | |
| 81kD | Prot | 16 ppm | 100 | — | — |
| | | 9.5 ppm | — | 25 | 2.1 mm |
| 17/20 | Ctrl | 5 ppm | — | 0 | 6 mm |
| Tril | Ctrl | — | 40 | 0 | 6 mm |

IA = IOWA, JH = JEALOTT'S HILL, CTRL = CONTROL
AVE SIZE = AVERAGE SIZE OF SURVIVING LARVAE

TABLE 18

81kD PROTEIN VERSUS COLORADO POTATO BEETLE

| | Control | Mono Q Fractions | | | | B.t. Strain |
|---|---|---|---|---|---|---|
| | | A | B | C | 81kD | 4580 |
| PREP 1 | | | | | | |
| Rate (ppm): | — | 330 | 213 | 270 | — | 40 |
| | 0 | 47 | 21 | 47 | — | 80 |
| PREP 2 | | | | | | |
| Rate (ppm): | — | 466 | 366 | 342 | 148 | 40 |
| | 0 | 87 | 67 | 87 | 33 | 100 |
| PREP 3 | | | | | | |
| Rate (ppm): | — | — | — | 588 | 257 | 40 |
| | 0 | — | — | 60 | 73 | 80 |

Results = % Mortality at 3 Days After Treatment

TABLE 19

81 kD PROTEIN VERSUS WESTERN CORN ROOTWORM

| | | % Mortality at: | |
|---|---|---|---|
| Sample | Rate | 3 DAT | 4 DAT |
| 81kD Protein | 900 ppm | 98 | 100 |
| Tris Control | — | 0 | 0 |
| Control (2) | — | 0 | 0 |

DAT = DAYS AFTER TREATMENT

We claim:

1. An insecticidal formulation for combating species of the order Lepidoptera and the genus *Diabrotica* which comprises as active ingredient an insecticidal δ-endotoxin produced by either of the strains JHCC 4353 and JHCC 4835.

2. An insecticidal formulation as claimed in claim 1 which further comprises a solid diluent of a surface active agent.

3. A process of protecting plants against attack by susceptible insects of the orders Coleoptera or Lepidoptera which comprises exposing such attacking insects to a δ-endotoxin produced by a strain JHCC 4853 or JHCC 4353 of *Bacillus thuringiensis*, deposited at the National Collections of Industrial and Marine Bacteria Scotland under the reference numbers 40091 or 40090 respectively.

4. A process as claimed in claim 3 which comprises treating the plants prior to or during such attack with insecticidally effective amounts of an insecticidal formulation for combating species of the order Lepidoptera and the genus *Diabrotica* which comprises as an active ingredient an insecticidal delta-endotoxin produced by either JHCC 4353 or JHCC 4835.

5. A process as claimed in claim 3 in which the plant is maize (corn).

6. A process as claimed in claim 3 in which the plant is potato, tomato, cotton, tobacco or cucurbit.

7. A process as claimed in claim 5 in which the insect is Western, Northern or Southern corn rootworm.

8. A process as claimed in claim 5 in which the insect is European corn borer or Corn earworm.

* * * * *